United States Patent [19]

Dressler

[11] Patent Number: 4,656,302
[45] Date of Patent: Apr. 7, 1987

[54] TRIS-(3-HYDROXY-4,6-DI-T-ALKYLPHE-NYL) PHOSPHITES

[75] Inventor: Hans Dressler, Monroeville, Pa.

[73] Assignee: Koppers Company, Inc., Pittsburgh, Pa.

[21] Appl. No.: 709,658

[22] Filed: Mar. 8, 1985

[51] Int. Cl.$^4$ ............................................. C07F 9/145
[52] U.S. Cl. .................................... 558/194; 524/150
[58] Field of Search ........................ 260/953; 524/150; 558/194

[56] References Cited

U.S. PATENT DOCUMENTS 2,058,343 10/1936 Moran et al. ................... 260/953 X
3,467,737 9/1969 Brindell et al. ...................... 260/953
4,440,696 4/1984 Maul et al. ........................... 260/976

FOREIGN PATENT DOCUMENTS 0049166 7/1982 European Pat. Off. .
2027713 11/1982 United Kingdom .

Primary Examiner—Anton H. Sutto
Attorney, Agent, or Firm—Daniel J. Long; Herbert J. Zeh, Jr.

[57] ABSTRACT

A group of phenolic phosphite compounds having the formula

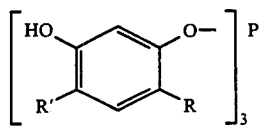

wherein R and R' may be the same or different and are tertiary alkyl groups containing from 4 to 12 carbon atoms. These compounds are disclosed to be useful as stabilizers and antioxidants in various organic materials.

1 Claim, No Drawings

TRIS-(3-HYDROXY-4,6-DI-T-ALKYLPHENYL) PHOSPHITES

1. FIELD OF THE INVENTION

The present invention relates to novel tris-hydroxyaryl phosphites which are useful as stabilizers and antioxidants for organic materials.

2. BRIEF DESCRIPTION OF THE PRIOR ART

It is known in the art that certain hindered phenolic phosphites are useful as stabilizers for organic materials. In particular, U.S. Pat. No. 3,407,737 discloses certain tertiary-alkyl-substituted-para-hydroxyphenyl phosphites having the formula $$(L-O-)_x(M-O-)_yP$$

wherein M is a hydrocarbon group, x is from 1 to 3, y is from 0 to 2, x plus y equals 3, and L is a teritary-alkyl-para-hydroxyphenyl group of the formula

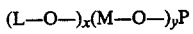

wherein R and R' are tertiary alkyl groups, n is 1 or 2, m is 0 or 1, and n plus m is not greater than 2. These compounds are disclosed to be useful as stabilizers for polypropylene or other polymers. Included in the compounds as disclosed are those in which y is 0, that is, those of the formula

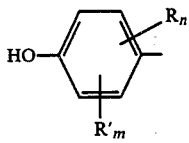

wherein R and R' are tertiary alkyl groups, n is 1 or 2, m is 0 or 1 and n plus m is not greater than 2. These compounds are disclosed to be useful as stabilizers for polypropylene or other polymers. When n is one and m is zero, the chemicals are derived from mono(tertiary-alkyl)hydroquinones, and the tertiary alkyl group may be in the 2- or 3-position in the phosphite, preferably in the 3-position. When n plus m equals two, the chemicals are derived from di(tertiary-alkyl)hydroquinones in which the tertiary alkyl groups are preferably in the 2- and 5-positions.

SUMMARY OF THE INVENTION

The present invention comprises a group of tris-(3-hydroxy-4,6-di-t-alkylphenyl)phosphite compounds having the formula

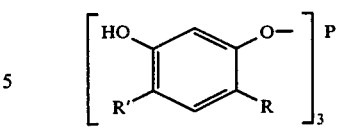

wherein R and R' may be the same or different and are tertiary alkyl groups containing from 4 to usually not more than 12 carbons atoms (e.g., tertiary-butyl, tertiary-pentyl t-octyl, t-dodecyl). These compounds are, surprisingly and unexpectedly, found to be useful as stabilizers and antioxidants for organic materials such as thermoplastics, elastomers, hydraulic fluids, fluid lubricants and greases. They are also found to have excellent thermal and hydrolytic stability.

The compounds of the present invention are preferably made from 4,6-di-t-butylresorcinol and phosphorus trichloride in the presence of pyridine, alkylpyridines, quinolines or aryl phosphines as the catalyst and aliphatic or aromatic hydrocarbons or halogenated hydrocarbons as the solvent.

The stabilizer and antioxidant of the present invention can be readily incorporated into plastic material by various standard procedures. In one technique the dry stabilizer in powdered form is mixed with a powdered or granular plastic and the mixture is mixed, milled, molded and/or extruded, at elevated temperatures if required. In another procedure an aqueous suspension or emulsion of finely divided polymeric material may be admixed with a suspension or emulsion of the stabilizing agent. Alternatively, it is possible to spray or mix a polymeric material in powdered or granular form with a solution or dispersion of the stabilizing agent in an appropriate solvent, such as hexane or xylene. It is also possible to incorporate the stabilizing agent in a finished article by introducing the plastic material into a bath containing the stabilzing agent in an appropriate liquid solvent and permitting the plastic material to remain in the bath for some time until the plastic has been properly treated. Thereafter, the material is dried to remove any of the remaining solvent. Plastic material in the form of fibers and films may also be sprayed with a solution or suspension of the stabilizing agent in a solvent or dispersant by any standard technique.

The plastic material should contain a stabilizing amount of the stabilizing agent; that is, the amount of stabilizing agent sufficient to prevent deterioration and embrittlement of the plastic material. The amount of stabilizing agent to be used will depend to a large extent upon the amount of exposure to which plastic is subjected and the nature of the plastic to be treated. The agent is generally added to an amount of between 0.01 to 5 percent by weight of the plastic material and preferably between 0.1 and 4 percent by weight.

As a stabilizing agent and antioxidant for plastics, the compounds of the present invention impart protection against heat and oxidation degradation to numerous plastic materials. These materials include polyethylene, polypropylene, polystyrene, polyvinyl acetate, polyvinylchloride, copolymers of vinyl chloride and vinylidene chloride, cellulose resins, such as nitrocellulose, ethylcellulose, and cellulose acetate, and numerous other materials. The agent can be used alone or together with other additives, such as fillers, pigments, etc.

The compounds of the invention may be used as the sole stabilizer or in mixture with other heat, oxidation

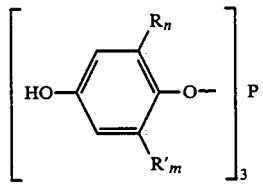

or light stabilizers, e.g., with other phenolic antioxidants, with thio-di-propionates, or with other phosphites.

DETAILED DESCRIPTION

The invention will be illustrated more clearly by the following examples.

EXAMPLE 1

To a stirred charge of 133.2 g. (0.6 m.) of 4,6-di-t-butylresorcinol, 200 ml. of xylene, and a catalytic amount of 2,4-lutidine (1.3 g.) was added dropwise, during 22 minutes, 28.0 g. (0.2 m.) of phosphorus trichloride at 40°–45° C. Shortly after the addition of $PCl_3$ was started, heavy evolution of hydrogen chloride began. The slurry was held at 40° C. for another 1.0 hr. A moderate flow of nitrogen was then started through the reactor and the charge was heated to 120° C. in 1.0 hr., then held at 120°–125° C. for 2.5 hrs. At the end of this period there was very little hydrogen chloride evolved. The mixture was cooled to 25° C. and filtered. The cake was washed with 50 ml. of xylene and vacuum-dried at 140° C. to give 92.3 g. of a white solid, a 66.5% yield of tris-(3-hydroxy-4,6-di-t-butylphenyl)phosphite, (hereinafter referred to as "Compound I"); m.p. (Mettler apparatus) 277.6° C.; elemental analysis: 4.4%P (calculated for I: 4.47%P). This compound shows some solubility in methanol, isopropanol, methyl isobutyl ketone and chlorotoluene.

EXAMPLE 2

To demonstrate the efficacy of the compounds of the present invention as high termperature process stabilizers for polypropylene, a sample of polypropylene (SHELL 55XX) was tumble-mixed with 0.05 percent by weight of Compound I, then mill-mixed for 10 min. at 171° C. (340° F.). A similar sample of SHELL 55XX polypropylene was tumble-mixed with 0.05 percent by weight of a known stabilizer, tetrakis[methylene 3-(3'-5'-di-t-butyl-4-hydroxphenyl)propionate]methane, which is commerically available from Ciba-Geigy Corporation under the trademark IRGANOX 1010 (hereinafter referred to as "Compound II"). The stocks were then removed from the rolls, cooled and chopped. The samples were then submitted to a multiple extrusion test (in a Brabender extruder) at 289° C. (550° F.), with melt index determinations being made on the polymer after each extrusion. The results are given in Table 1. It will be seen from Table I that Compound I was clearly superior.

TABLE I

| Additive | Melt Index (g./10 min.) No. of Extrusions | | | | | Initial Color |
|---|---|---|---|---|---|---|
| | 0 | 1 | 2 | 3 | 4 | |
| Compound I | 7.3 | 7.8 | 13.5 | 23.3 | 36.2 | Off-white |
| Compound II | 7.1 | 9.4 | 18.9 | 45.4 | 69.0 | Off-white |

EXAMPLE 3

To demonstrate the efficacy of the compound of the present invention as both a long term heat stabilizer and an antioxidant for polypropylene, a sample strip of polypropylene containing about 0.15 percent by weight Compound I and having dimensions of 0.25 inches by 2.0 inches by 0.02 inches was bent around an ⅛ inch diameter mandrel in a circulatory air oven, the temperature of which was maintained at about 130° C. This sample passed 800 hours of such exposure without failure.

EXAMPLE 4

To demonstrate the efficacy of the compounds of the present invention as an antioxidant for lubricants, SAE 10 mineral oil was mixed with Compound I. The mixture was 1 percent by weight Compound I. At 177° C. (350° F.) in air; and after 24 hours there was no visible sludge formation and only a slight color change. After 48 hrs. the color was dark, but there still no sludge formation. A sample of this SAE 10 mineral oil without Compound I showed considerable sludge formation under the same conditions.

EXAMPLE 5

A 50-gal. reactor was charged with 164.5 lb. heptane, 263 g. of triphenylphosphine as the catalyst, and 112.5 lb. of 4,6-di-t-butylresorcinol. The stirred charge was purged with nitrogen at 0.4 CFM, heated to 40° C., and 24.26 lb. of phosphorous trichloride was added during 20 minutes. When the evolution of HCl gas subsided (after 3 hrs.), the charge was purged with nitrogen at 0.7 CFM, heated to 90° C. (boiling point), and refluxed for 2 hrs. Finally, the reactor was cooled to 3°–5° C. and the slurry was centrifuged. The wet cake of product was washed with heptane and dried at 115° C./38 Torr to give 104.0 lb. (88.7% yield) of white product, capillary m.p. 286° C.

What is claimed is:
1. The compound tris-(3-hydroxy-4,6-di-t-butylphenyl)phosphite.

* * * * *